(12) United States Patent
Tanaka et al.

(10) Patent No.: US 8,348,906 B2
(45) Date of Patent: Jan. 8, 2013

(54) ASPIRATOR FOR PNEUMOSTOMA MANAGEMENT

(75) Inventors: Don Tanaka, Saratoga, CA (US);
Joshua P. Wiesman, Boston, MA (US);
David C. Plough, Portola Valley, CA (US)

(73) Assignee: Portaero, Inc., Cupertino, CA (US)

( * ) Notice: Subject to any disclaimer, the term of this patent is extended or adjusted under 35 U.S.C. 154(b) by 523 days.

(21) Appl. No.: 12/388,461

(22) Filed: Feb. 18, 2009

(65) Prior Publication Data

US 2009/0209917 A1    Aug. 20, 2009

Related U.S. Application Data

(60) Provisional application No. 61/029,830, filed on Feb. 19, 2008, provisional application No. 61/032,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009.

(51) Int. Cl.
*A61M 5/178* (2006.01)
*A61M 1/00* (2006.01)
*A61M 5/32* (2006.01)
*A61M 31/00* (2006.01)
*A61M 16/00* (2006.01)
*A61B 17/32* (2006.01)

(52) U.S. Cl. ............ 604/212; 604/35; 604/37; 604/174; 604/275; 604/276; 128/207.14; 606/108

(58) Field of Classification Search ............... 604/99.04, 604/104, 174, 275, 246, 212, 180, 167.03, 604/319, 35, 37, 118, 276; 128/202.28, 278, 128/207.14–207.15; 606/108, 167
See application file for complete search history.

(56) References Cited

U.S. PATENT DOCUMENTS 733,152 A    7/1903   Chisholm
(Continued)

FOREIGN PATENT DOCUMENTS

EP      0260543 A1    3/1988
(Continued)

OTHER PUBLICATIONS

Rendina et al., "Feasibility and safety of the airway bypass procedure for patients with emphysema", The Journal of Thoracic and Cardiovascular Surgery 2003; 125: 1294-1299.

(Continued)

*Primary Examiner* — Kevin C Sirmons
*Assistant Examiner* — Bradley G Thomas, Jr.
(74) *Attorney, Agent, or Firm* — Fliesler Meyer LLP

(57) ABSTRACT

A pneumostoma management system includes a pneumostoma management device for maintaining the patency of a pneumostoma while controlling the flow of material through the pneumostoma and a pneumostoma aspirator for pneumostoma care. The pneumostoma aspirator includes a bulb or syringe for applying positive or negative pressure, a tube for entering the pneumostoma and a limiting device for limiting the depth of insertion of the tube into a pneumostoma. The pneumostoma aspirator may also be used to introduce irrigation fluid into the pneumostoma and/or remove irrigation fluid and discharge from the pneumostoma.

25 Claims, 9 Drawing Sheets

U.S. PATENT DOCUMENTS

| | | | |
|---|---|---|---|
| 953,922 A | 4/1910 | Rogers | |
| 2,206,687 A | 7/1940 | Bloomheart | |
| 2,867,213 A | 1/1959 | Thomas, Jr. | |
| 2,873,742 A | 2/1959 | Shelden | |
| 2,991,787 A | 7/1961 | Shelden et al. | |
| 3,101,712 A * | 8/1963 | Strazdins et al. | 604/218 |
| 3,253,594 A | 5/1966 | Matthews et al. | |
| 3,384,087 A | 5/1968 | Brummelkamp | |
| 3,463,159 A | 8/1969 | Heimlich | |
| 3,511,243 A | 5/1970 | Toy | |
| 3,556,103 A | 1/1971 | Calhoun et al. | |
| 3,638,649 A | 2/1972 | Ersek | |
| 3,682,166 A | 8/1972 | Jacobs | |
| 3,688,773 A | 9/1972 | Weiss | |
| 3,707,146 A | 12/1972 | Cook et al. | |
| 3,766,920 A | 10/1973 | Greene | |
| 3,777,757 A * | 12/1973 | Gray et al. | 604/99.04 |
| 3,788,326 A | 1/1974 | Jacobs | |
| 3,817,250 A | 6/1974 | Weiss et al. | |
| 3,908,704 A | 9/1975 | Clement et al. | |
| 3,916,903 A | 11/1975 | Pozzi | |
| 4,153,058 A * | 5/1979 | Nehme | 604/167.03 |
| 4,291,694 A | 9/1981 | Chai | |
| 4,439,189 A | 3/1984 | Sargeant et al. | |
| 4,465,062 A | 8/1984 | Versaggi et al. | |
| 4,502,482 A | 3/1985 | DeLuccia et al. | |
| 4,583,977 A | 4/1986 | Shishov et al. | |
| 4,664,660 A | 5/1987 | Goldberg et al. | |
| 4,799,494 A | 1/1989 | Wang | |
| 4,813,929 A | 3/1989 | Semrad | |
| 4,826,495 A | 5/1989 | Petersen | |
| 4,828,553 A | 5/1989 | Nielsen | |
| 4,869,717 A | 9/1989 | Adair | |
| 4,872,869 A | 10/1989 | Johns | |
| 4,889,534 A | 12/1989 | Mohiuddin et al. | |
| 4,931,045 A | 6/1990 | Steer | |
| 4,944,724 A | 7/1990 | Goldberg et al. | |
| 4,959,054 A | 9/1990 | Heimke et al. | |
| 4,976,688 A | 12/1990 | Rosenblum | |
| 5,004,456 A | 4/1991 | Botterbusch et al. | |
| 5,060,645 A | 10/1991 | Russell | |
| 5,078,689 A | 1/1992 | Keller | |
| 5,137,509 A | 8/1992 | Freitas | |
| 5,139,485 A | 8/1992 | Smith et al. | |
| 5,218,957 A | 6/1993 | Strickland | |
| 5,230,332 A | 7/1993 | Strickland | |
| 5,230,350 A | 7/1993 | Fentress | |
| 5,261,708 A | 11/1993 | Steer | |
| 5,263,939 A | 11/1993 | Wortrich | |
| 5,312,331 A | 5/1994 | Knoepfler | |
| 5,315,992 A | 5/1994 | Dalton | |
| 5,336,206 A | 8/1994 | Shichman | |
| 5,354,283 A | 10/1994 | Bark et al. | |
| 5,356,386 A | 10/1994 | Goldberg et al. | |
| 5,366,478 A | 11/1994 | Brinkerhoff et al. | |
| 5,370,625 A | 12/1994 | Shichman | |
| 5,376,376 A | 12/1994 | Li | |
| 5,389,077 A | 2/1995 | Melinyshyn et al. | |
| 5,401,262 A | 3/1995 | Karwoski et al. | |
| 5,403,264 A | 4/1995 | Wohlers et al. | |
| 5,431,633 A | 7/1995 | Fury | |
| 5,478,333 A | 12/1995 | Asherman, Jr. | |
| 5,484,401 A | 1/1996 | Rodriguez et al. | |
| 5,496,297 A | 3/1996 | Olsen | |
| 5,501,677 A | 3/1996 | Jensen | |
| 5,501,678 A | 3/1996 | Olsen | |
| 5,588,424 A | 12/1996 | Insler et al. | |
| 5,616,131 A | 4/1997 | Sauer et al. | |
| 5,660,175 A | 8/1997 | Dayal | |
| 5,662,629 A | 9/1997 | Steer et al. | |
| 5,728,066 A | 3/1998 | Daneshvar | |
| 5,730,735 A | 3/1998 | Holmberg et al. | |
| 5,738,661 A | 4/1998 | Larice | |
| 5,807,341 A | 9/1998 | Heim | |
| 5,830,200 A | 11/1998 | Steer et al. | |
| 5,843,053 A | 12/1998 | Steer | |
| 5,897,531 A * | 4/1999 | Amirana | 604/180 |
| 5,931,821 A | 8/1999 | Weilbacher et al. | |
| 5,954,636 A | 9/1999 | Schwartz et al. | |
| 5,971,962 A | 10/1999 | Kojima et al. | |
| 5,972,026 A | 10/1999 | Laufer et al. | |
| 6,056,744 A | 5/2000 | Edwards | |
| 6,059,816 A | 5/2000 | Moenning | |
| 6,083,255 A | 7/2000 | Laufer et al. | |
| 6,174,323 B1 | 1/2001 | Biggs et al. | |
| 6,197,010 B1 | 3/2001 | Leise, Jr. et al. | |
| 6,200,333 B1 | 3/2001 | Laufer | |
| 6,258,100 B1 | 7/2001 | Alferness et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,293,930 B1 | 9/2001 | Brunsgaard et al. | |
| 6,293,951 B1 | 9/2001 | Alferness et al. | |
| 6,299,633 B1 | 10/2001 | Laufer | |
| 6,322,536 B1 | 11/2001 | Rosengart et al. | |
| 6,328,689 B1 | 12/2001 | Gonzalez et al. | |
| 6,330,882 B1 | 12/2001 | French | |
| 6,334,441 B1 | 1/2002 | Zowtiak et al. | |
| 6,358,269 B1 | 3/2002 | Aye | |
| 6,398,775 B1 | 6/2002 | Perkins et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,432,100 B1 | 8/2002 | Affeld | |
| 6,443,156 B1 | 9/2002 | Niklason et al. | |
| 6,468,292 B1 | 10/2002 | Mollenauer et al. | |
| 6,485,407 B2 | 11/2002 | Alferness et al. | |
| 6,488,673 B1 | 12/2002 | Laufer et al. | |
| 6,491,706 B1 | 12/2002 | Alferness et al. | |
| 6,514,290 B1 | 2/2003 | Loomas | |
| 6,517,519 B1 | 2/2003 | Rosen et al. | |
| 6,520,183 B2 | 2/2003 | Amar | |
| 6,527,761 B1 | 3/2003 | Soltesz et al. | |
| 6,550,475 B1 | 4/2003 | Oldfield | |
| 6,569,121 B1 | 5/2003 | Purow et al. | |
| 6,569,166 B2 | 5/2003 | Gonzalez | |
| 6,585,639 B1 | 7/2003 | Kotmel et al. | |
| 6,589,161 B2 | 7/2003 | Corcoran | |
| 6,592,594 B2 | 7/2003 | Rimbaugh et al. | |
| 6,599,311 B1 | 7/2003 | Biggs et al. | |
| 6,609,521 B1 | 8/2003 | Belani et al. | |
| 6,629,951 B2 | 10/2003 | Laufer et al. | |
| 6,632,239 B2 | 10/2003 | Snyder et al. | |
| 6,632,243 B1 | 10/2003 | Zadno-Azizi et al. | |
| 6,634,360 B1 | 10/2003 | Flodin | |
| 6,634,363 B1 | 10/2003 | Danek et al. | |
| 6,638,253 B2 | 10/2003 | Breznock | |
| 6,653,525 B2 | 11/2003 | Ingenito et al. | |
| 6,659,961 B2 | 12/2003 | Robinson | |
| 6,679,264 B1 | 1/2004 | Deem et al. | |
| 6,682,506 B1 | 1/2004 | Navarro | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,712,812 B2 | 3/2004 | Roschak et al. | |
| 6,736,797 B1 | 5/2004 | Larsen et al. | |
| 6,749,606 B2 | 6/2004 | Keast et al. | |
| 6,770,063 B2 | 8/2004 | Goldberg et al. | |
| 6,770,070 B1 | 8/2004 | Balbierz | |
| 6,790,172 B2 | 9/2004 | Alferness et al. | |
| 6,827,086 B2 | 12/2004 | Shuman | |
| 6,837,906 B2 | 1/2005 | Ginn | |
| 6,840,243 B2 | 1/2005 | Deem et al. | |
| 6,843,767 B2 | 1/2005 | Corcoran et al. | |
| 6,846,292 B2 | 1/2005 | Bakry | |
| 6,849,061 B2 | 2/2005 | Wagner | |
| 6,852,108 B2 | 2/2005 | Barry et al. | |
| 6,860,847 B2 | 3/2005 | Alferness et al. | |
| 6,878,141 B1 | 4/2005 | Perkins et al. | |
| 6,886,558 B2 | 5/2005 | Tanaka | |
| 6,901,927 B2 | 6/2005 | Deem et al. | |
| 6,904,909 B2 | 6/2005 | Andreas et al. | |
| 6,905,518 B2 | 6/2005 | Ginn | |
| 6,916,310 B2 | 7/2005 | Sommerich | |
| 6,929,637 B2 | 8/2005 | Gonzalez et al. | |

| Patent/Publication | Date | Inventor |
|---|---|---|
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,377,278 B2 | 5/2008 | Tanaka |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0117173 A1* | 8/2002 | Lynn et al. ............... 128/202.28 |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1* | 2/2004 | Tanaka ..................... 604/104 |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0079838 A1 | 4/2006 | Walker et al. |
| 2006/0095002 A1 | 5/2006 | Soltesz et al. |

| | | | |
|---|---|---|---|
| 2006/0107961 A1 | 5/2006 | Tanaka | |
| 2006/0116749 A1 | 6/2006 | Willink et al. | |
| 2006/0118125 A1 | 6/2006 | Tanaka | |
| 2006/0118126 A1 | 6/2006 | Tanaka | |
| 2006/0124126 A1 | 6/2006 | Tanaka | |
| 2006/0130830 A1 | 6/2006 | Barry | |
| 2006/0135947 A1 | 6/2006 | Soltesz et al. | |
| 2006/0135984 A1 | 6/2006 | Kramer et al. | |
| 2006/0142672 A1 | 6/2006 | Keast et al. | |
| 2006/0161233 A1 | 7/2006 | Barry et al. | |
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |
| 2007/0299424 A1 | 12/2007 | Cumming et al. | |
| 2008/0281151 A1 | 11/2008 | Chang et al. | |
| 2008/0281295 A1 | 11/2008 | Chang et al. | |
| 2008/0281433 A1 | 11/2008 | Chang et al. | |
| 2008/0283065 A1 | 11/2008 | Chang et al. | |
| 2008/0287878 A1 | 11/2008 | Tanaka | |
| 2008/0287973 A1 | 11/2008 | Aster et al. | |
| 2008/0295829 A1 | 12/2008 | Evens | |
| 2009/0205641 A1 | 8/2009 | Tanaka | |
| 2009/0205643 A1 | 8/2009 | Tanaka et al. | |
| 2009/0205644 A1 | 8/2009 | Tanaka et al. | |
| 2009/0205645 A1 | 8/2009 | Tanaka et al. | |
| 2009/0205646 A1 | 8/2009 | Tanaka et al. | |
| 2009/0205647 A1 | 8/2009 | Plough et al. | |
| 2009/0205648 A1 | 8/2009 | Tanaka et al. | |
| 2009/0205649 A1 | 8/2009 | Tanaka et al. | |
| 2009/0205650 A1 | 8/2009 | Tanaka et al. | |
| 2009/0205651 A1 | 8/2009 | Tanaka et al. | |
| 2009/0205658 A1 | 8/2009 | Tanaka et al. | |
| 2009/0205665 A1 | 8/2009 | Tanaka et al. | |
| 2009/0209856 A1 | 8/2009 | Tanaka et al. | |
| 2009/0209906 A1 | 8/2009 | Tanaka et al. | |
| 2009/0209909 A1 | 8/2009 | Tanaka et al. | |
| 2009/0209917 A1 | 8/2009 | Tanaka et al. | |
| 2009/0209924 A1 | 8/2009 | Tanaka | |
| 2009/0209936 A1 | 8/2009 | Tanaka et al. | |
| 2009/0209970 A1 | 8/2009 | Tanaka et al. | |
| 2009/0209971 A1 | 8/2009 | Tanaka et al. | |
| 2010/0211032 A1* | 8/2010 | Tsai et al. | 604/319 |

FOREIGN PATENT DOCUMENTS

| | | |
|---|---|---|
| EP | 1358904 | 5/2003 |
| EP | 1658867 | 5/2006 |
| EP | 1815821 | 8/2007 |
| EP | 2242527 | 10/2010 |
| JP | 62-2028747 U | 6/1986 |
| JP | 2000197706 | 7/2000 |
| RU | 2192185 | 10/2002 |
| WO | WO 96/39960 | 12/1996 |
| WO | WO 99/66975 | 12/1999 |
| WO | WO 00/76577 A1 | 12/2000 |
| WO | WO 01/45568 A1 | 6/2001 |
| WO | WO2005070480 | 8/2005 |

OTHER PUBLICATIONS

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000: 1-11, retrieved from <http://www.scielo.br/scielo.php?script=arttext&pid=S0102-35862000000300003&Ing=e . . . > May 2, 2007.

Shah, Pallav, "Surgical and Non-surgical Volume Reduction for COPD", Presented at the Clinical Consensus on COPD, Mar. 2-3, 2007, Novotel London West, 56 pages; see p. 55 of 56.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woolcock et al., "Mechanical factors influencing collateral ventilation in human, dog, and pig lungs", Journal of Applied Physiology 1971, 30: 99-115.

Woodring et al., "Pneumothorax ex vacuo", Chest 1996, 110: 1102-1124.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1:115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.

International Search Report for PCT/US2009/034322 dated Oct. 5, 2009; 14 pages.

International Search Report for PCT/US2009/034406 dated Dec. 2, 2009; 16 pages.

Aljuri et al., "Validation and pilot clinical study of a new bronchoscopic method to measure collateral ventilation before endobronchial lung volume reduction", J Appl Physio 106: 774-783, 2009.

Al-Salem et al., "Computed tomography-guided percutaneous needle aspiration of lung abscesses in neonates and children", Pediatr Surg Int (1997) 12: 417-419, copyright Springer-Verlag 1997.

Ball, Jr et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.

Brenner et al., "Innovative Approaches to Lung Volume Reduction for Emphysema", Chest 2004; 126: 238-248.

Brutinel et al., "A two-year experience with the neodymium-YAG laser in endobronchial obstruction", Chest 1987; 91: 159-165.

Celli et al. "Standards for the diagnosis and treatment of patients with COPD: a summary of the ATS/ERS position paper", European Respiratory Journal 2004; 23; 932-946.

Cetti et al., "Collateral ventilation", Thorax 2006; 61: 371-373.

Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System.

Choong et al., "Feasibility and safety of airway bypass stent placement and influence of topical mitomycin C on stent patency", The Journal of Thoracic and Cardiovascular Surgery 2005; 129: 632-638.

Choong et al., "Transpleural ventilation of explanted human lungs", Thorax 2007; 62: 623-630; originally published online Apr. 5, 2007.

Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.

Dumon, J. F., "A Dedicated Tracheobronchial Stent", Chest 1990; 97: 328-332.

Eloesser, "An Operation for Tuberculous Empyema", Chest 1935; 1: 8-23.

Fein, Alan M, "Lung volume Reduction Surgery: Answering the Crucial Questions", Chest 1998; 113: 277-282.

Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.

Fessler, Henry E., "Collateral Ventilation, the Bane of Bronchoscopic Volume Reduction", Am J Respir Crit Care Med 2005; 171: 423-425.

Frawley et al., "Airway Pressure Release Ventilation: Theory and Practice", AACN Clinical Issues 2001; vol. 12, No. 2: 234-246.

Freitag et al., "Theoretical and experimental basis for the development of a dynamic airway stent", European Respiratory Journal 1994; 7: 2038-2045.

Ghaye et al., "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.

Goldstraw et al., "The Surgical Treatment of Emphysema: The Brompton Approach", Chest Surgery Clinics of North America Nov. 1995; vol. 5, No. 4: 777-797.

Habashi, Nader M., "Other approaches to open-lung ventilation: Airway pressure release ventilation", Crit Care Med 2005, vol. 33, No. 3 (Suppl): S228-S240.

Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.

Heimlich, Henry J., "Respiratory Rehabilitation with Transtracheal Oxygen System", Ann Otol Rhinol Laryngol Nov./Dec. 1982; 91: 643-647.

Hogg et al., "Chronic obstructive pulmonary disease c2: Pathology and biochemistry of emphysema", Thorax 2002; 57: 830-834.

Hogg et al., "The Resistance of Collateral Channels in Excised Human Lungs", Journal of Clinical Investigation 1969; 48: 421-431.

Joannette, Albert, "Drainage of Tuberculous Cavities by Aspiration (Monaldi Method)", The Canadian Medical Association Journal Jan. 1941; 46-48.

Korpela et al., "Bioabsorbable Self-reinforced Poly-L-Lactide, Metallic, and Silicone Stents in the Management of Experimental Tracheal Stenosis", Chest 1999; 115: 490-495.

Lausberg et al., "Bronchial Fenestration Improves Expiratory Flow in Emphysematous Human Lungs", Annals of Thoracic Surgery 2003; 75: 393-398.

Lorenzo et al., "Lung Abscesses in Children: Diagnostic and Therapeutic Needle Aspiration", Radiology Oct. 1985; 157: 79-80.

MacArthur et al., "Intracavity suction and drainage in the treatment of emphysematous bullae", Thorax 1977; 32: 668-672.

MacKlem, Peter T., "Collateral Ventilation", The New England Journal of Medicine Jan. 5, 1978; 298(1): 49-50.

Matson et al., "Evaluation of Various Surgical Procedures in the Treatment of Pulmonary Tuberculosis", Chest 1946; 12: 40-47.

McCoy, Robert, "Oxygen-Conserving Techniques and Devices", Respiratory Care Jan. 2000, vol. 45, No. 1: 95-104.

Meyers et al., "Chronic obstructive pulmonary disease 10: Bullectomy, lung volume reduction surgery, and transplantation for patients with chronic obstructive pulmonary disease", Thorax 2003; 58: 634-638.

Mined et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

U.S. Department of Health and Human Services; National Institutes of Health National Heart, Lung, and Blood Institute; "Chronic Obstructive Pulmonary Disease", NIH Publication No. Mar. 5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction" European Respiratory Review 2006; 15(100): 99-103.

Extended European Search Report dated Jun. 22, 2011 for PCT/US2009034374, 7 pages.

Extended European Search Report dated Jun. 15, 2011 for PCT/US2009034322, 7 pages.

Extended European Search Report dated Sep. 16, 2011 for PCT/US2009034380, 8 pages.

* cited by examiner

ASPIRATOR FOR PNEUMOSTOMA MANAGEMENT

CLAIM TO PRIORITY

This application claims priority to all of the following applications including: U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446, filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,460, filed Feb. 13, 2009, entitled "PNEUMOSTOMA MANAGEMENT SYSTEM HAVING A COSTMETIC AND/OR PROTECTIVE COVER"

U.S. patent application Ser. No. 12/388,455, filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,462, filed Feb. 18, 2009, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,453, filed Feb. 18, 2009, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, entitled "MULTI-LAYER PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE"; and U.S. patent application Ser. No. 12/388,470, filed Feb. 18, 2009, entitled "SELF-SEALING DEVICE AND METHOD FOR DELIVERY OF A THERAPEUTIC AGENT THROUGH A PNEUMOSTOMA".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema and is accepted by physicians and patients.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The stable artificial aperture into the lung through the chest is referred to herein as a pneumostoma. A pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing or sealing off a portion of the lung.

In some situations, mucus/discharge and/or foreign matter may accumulate in the pneumostoma or a medical device implanted in the pneumostoma. An aspirator and methods of use in accordance with embodiments of the present invention are desirable and useful to remove the mucus/discharge and/ or foreign matter in order to maintain the patency of the pneumostoma and prevent infection.

In accordance with a general embodiment the present invention provides a pneumostoma aspirator and methods for removing the mucus/discharge and/or foreign matter from a pneumostoma. Some embodiments, of the present invention may also be used to irrigate the pneumostoma instead of or in addition to providing suction.

In accordance with one embodiment, the present invention provides a pneumostoma management system which includes a partially-implantable pneumostoma vent, a chest mount and a pneumostoma aspirator. The pneumostoma aspirator attaches to the pneumostoma management device to safely and effectively apply suction to a pneumostoma.

In accordance with one embodiment, the present invention provides pneumostoma management system which includes a partially-implantable pneumostoma management device which can be placed into a pneumostoma to prevent the entry of foreign substances into the lung, control air flow through the pneumostoma and collect any materials that may exit the lung and a pneumostoma aspirator which attaches to the pneumostoma management device to safely and effectively apply suction to a pneumostoma.

In accordance with one embodiment, the present invention provides a pneumostoma management system which includes a partially-implantable pneumostoma vent, a chest mount and pneumostoma aspirator. The chest mount is secured to the skin of the patient. The partially-implantable pneumostoma vent is placed into a pneumostoma through an aperture in the chest mount. The pneumostoma aspirator attaches to the chest mount in the absence of the pneumostoma vent.

Thus, various systems, components and methods are provided for managing a pneumostoma and thereby treating COPD. Other objects, features and advantages of the invention will be apparent from drawings and detailed description to follow.

BRIEF DESCRIPTION OF THE DRAWINGS

The above and further features, advantages and benefits of the present invention will be apparent upon consideration of the present description taken in conjunction with the accompanying drawings.

FIG. 4A shows a perspective view of an alternative pneumostoma aspirator according to an embodiment of the present invention.

DETAILED DESCRIPTION OF THE INVENTION

Figure 1A:
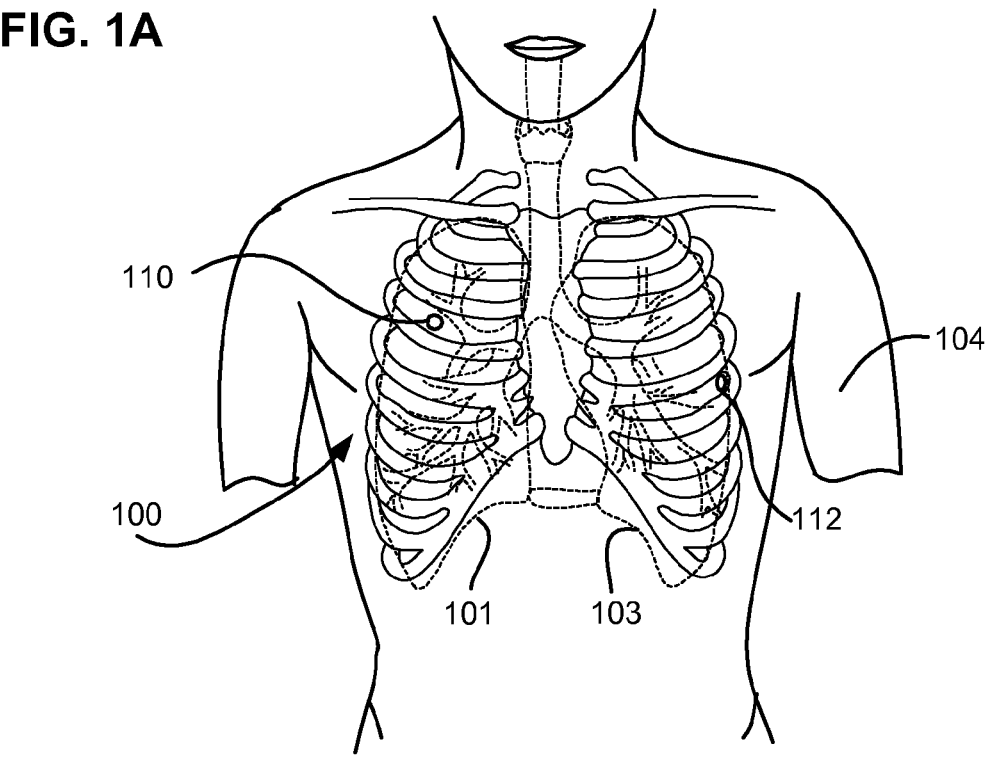
FIG. 1A shows the chest of a patient indicating alternative locations for a pneumostoma that may be managed using the device and methods of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Formation and Anatomy

FIG. 1A shows the chest of a patient identifying alternative locations for creating a pneumostoma that may be managed using the system of the present invention. A first pneumostoma 110 is shown on the front of the chest 100 over the right lung 101 (shown in dashed lines). The pneumostoma is preferably positioned over the third intercostal space on the midclavicular line. Thus the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis. Methods for forming the channel, opening, anastomosis and pleurodesis are disclosed in applicant's pending and issued patents and applications including U.S. patent application Ser. No. 10/881,408 entitled "Methods and Devices to Accelerate Wound Healing in Thoracic Anastomosis Applications" and U.S. patent application Ser. No.

12/030,006 entitled "Variable Parietal/Visceral Pleural Coupling" which are incorporated herein by reference in their entirety.

Figure 1B:
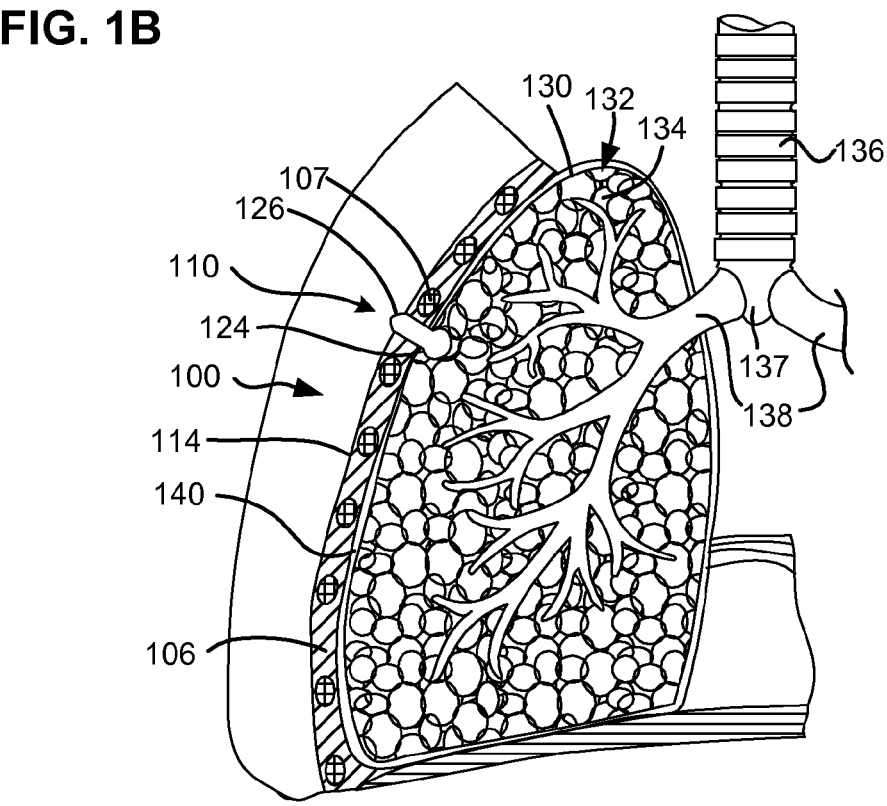
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 138. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

Figure 1C:
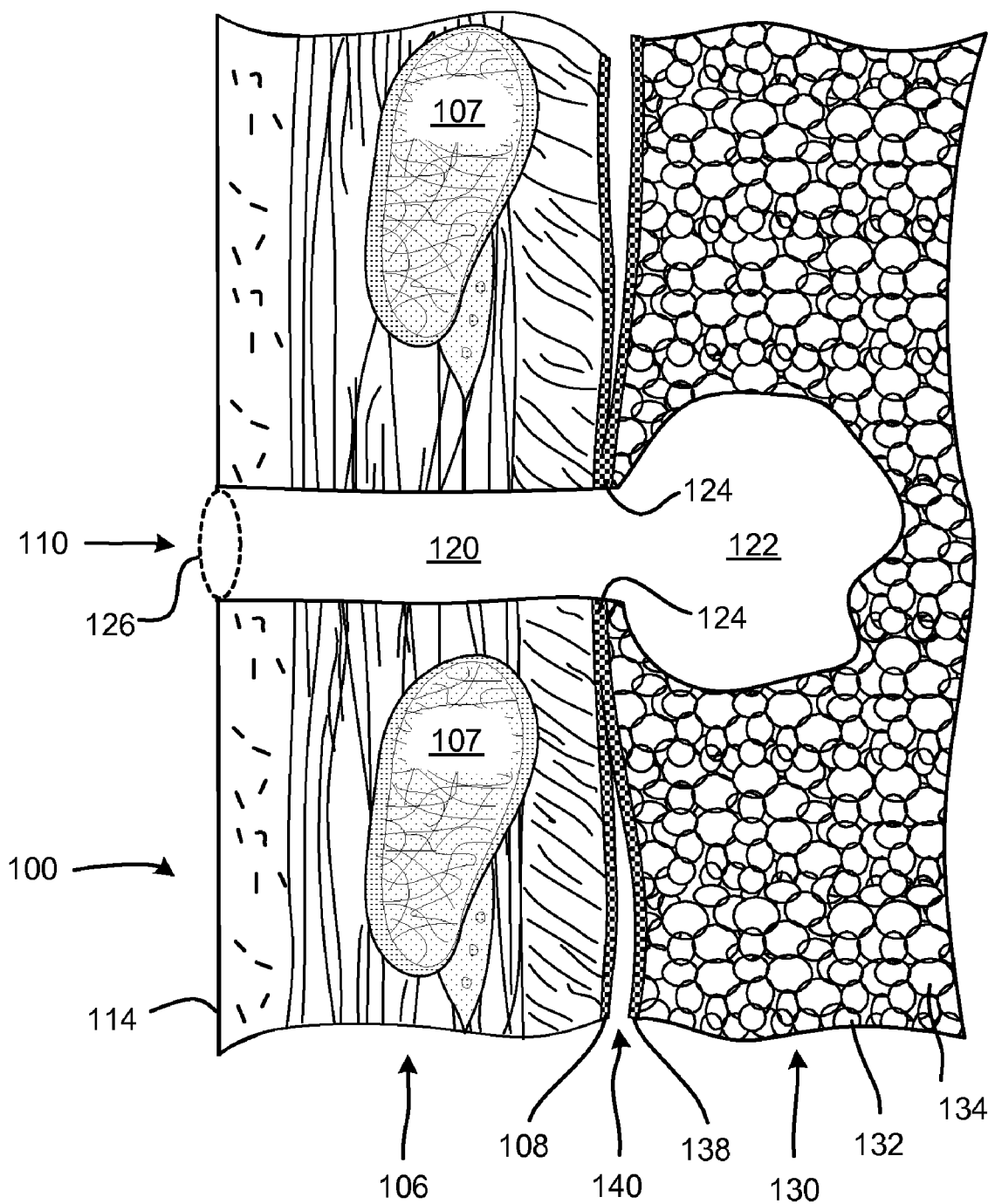
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the seal or adhesion surrounding the channel 120 where it enters the lung 130 which may comprise a pleurodesis 124. A pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the pleurodesis is preferably localized to the region surrounding the channel 120. The pleurodesis 124 surrounding the channel 120 prevents air from entering the pleural cavity 140. If air is permitted to enter pleural cavity 140, a pneumothorax will result and the lung may collapse.

Pleurodesis 124 can be created between the visceral pleura of the lung and the inner wall of the thoracic cavity using chemical methods including introducing into the pleural space irritants such as iodopovidone or silver nitrate, antibiotics (e.g. Doxycycline or Quinacrine), anticancer drugs (e.g. Bleomycin, Mitoxantrone or Cisplatin), cytokines (e.g. interferon alpha-2β and Transforming growth factor-β); pyrogens (e.g. *Corynebacterium parvum, Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedure is called dry abrasion pleurodesis. A pleurodesis may also be created using radiotherapy methods, including radioactive gold or external radiation. These methods cause an inflammatory response and or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop into pleurodesis over time. A range of biocompatible glues are available that may be used on the lung, including light-activatable glues, fibrin glues, cyanoacrylates and two part polymerizing glues. Applicant's copending U.S. patent application Ser. No. 12/030,006 entitled "VARIABLE PARIETAL/VISCERAL PLEURAL COUPLING" discloses methods such as pleurodesis for coupling a channel through the chest wall to the inner volume of the lung without causing a pneumothorax and is incorporated herein by reference for all purposes.

When formed, pneumostoma 110 provides an extra pathway for exhaled air to exit the lung 130 reducing residual volume and intra-thoracic pressure without the air passing through the major natural airways such as the bronchi 138 and trachea. Collateral ventilation is particularly prevalent in an emphysemous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110 thus makes use of collateral ventilation to collect air in cavity 122 and vent the air outside the body via channel 120 reducing residual volume and intra-thoracic pressure and bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Pneumostoma 110 thus achieves many of the advantages sought by lung volume reduction surgery without surgically removing a portion of the lung or sealing off a portion of the lung.

Applicants have found that a pneumostoma management system in accordance with embodiments of the present invention is desirable to maintain the patency of the pneumostoma and control flow of materials between the exterior of the patient and the parenchymal tissue of the lung via a pneumostoma. In accordance with embodiments of the present invention, the pneumostoma management system includes a pneumostoma management device and a pneumostoma aspirator as described herein.

Pneumostoma Management System Including A Pneumostoma Aspirator

As described above, a pneumostoma may be created to treat the symptoms of chronic obstructive pulmonary disease. A patient is typically provided with a pneumostoma management system to protect the pneumostoma and keeps the pneumostoma open on a day-to-day basis. In general terms a pneumostoma management device ("PMD") comprises a tube which is inserted into the pneumostoma and an external component which is secured to the skin of the patient to keep the tube in place. Gases escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube. Additional details and variations of pneumostoma management devices are described in applicant's pending and issued patents and applications including those related cases incorporated by reference above.

Figure 2A:
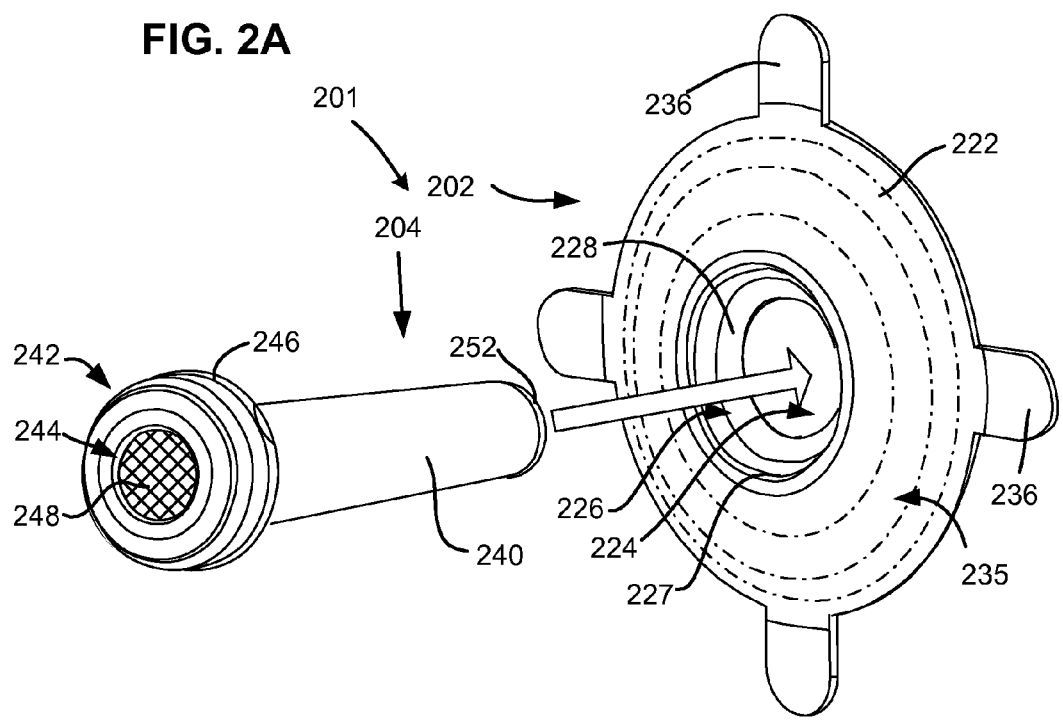
FIG. 2A shows a perspective view of components of a pneumostoma management device according to an embodiment of the present invention.
Figure 2B:
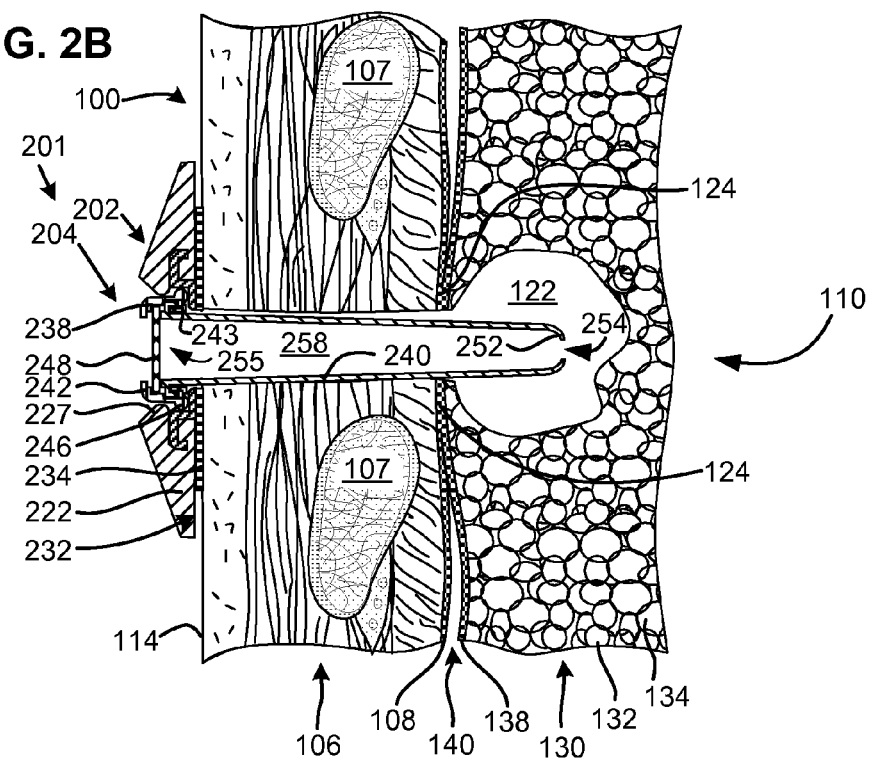
FIG. 2B shows a sectional view of the pneumostoma management device of FIG. 2A partially implanted in a pneumostoma.
Figure 2C:
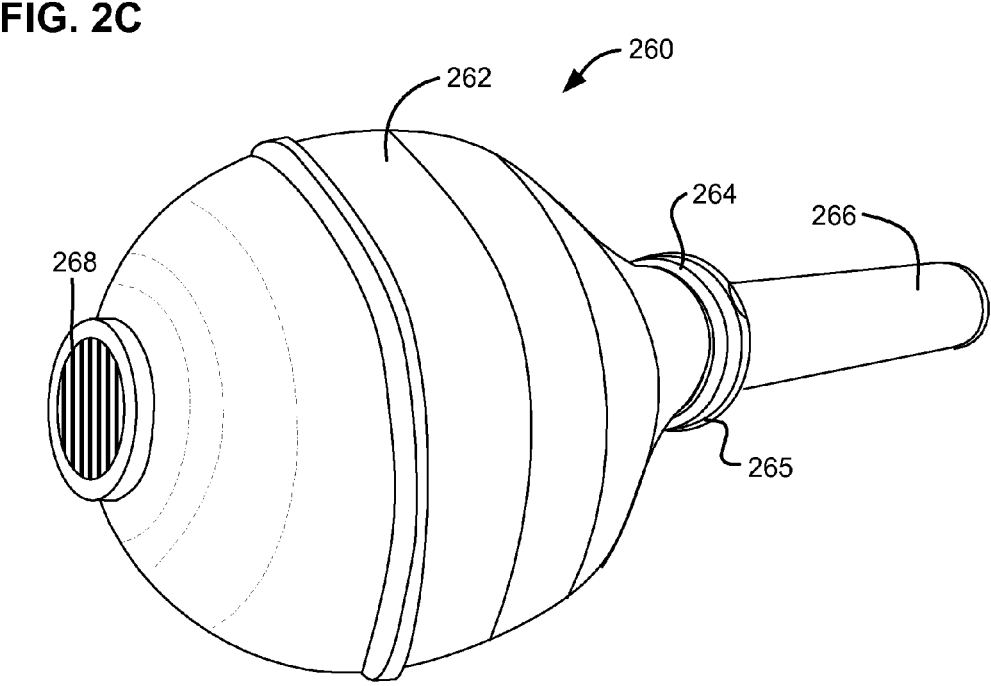
FIG. 2C shows a perspective view of a pneumostoma aspirator designed to operate with the pneumostoma management device of FIGS. 2A and 2B according to an embodiment of the present invention.
Figure 2D:
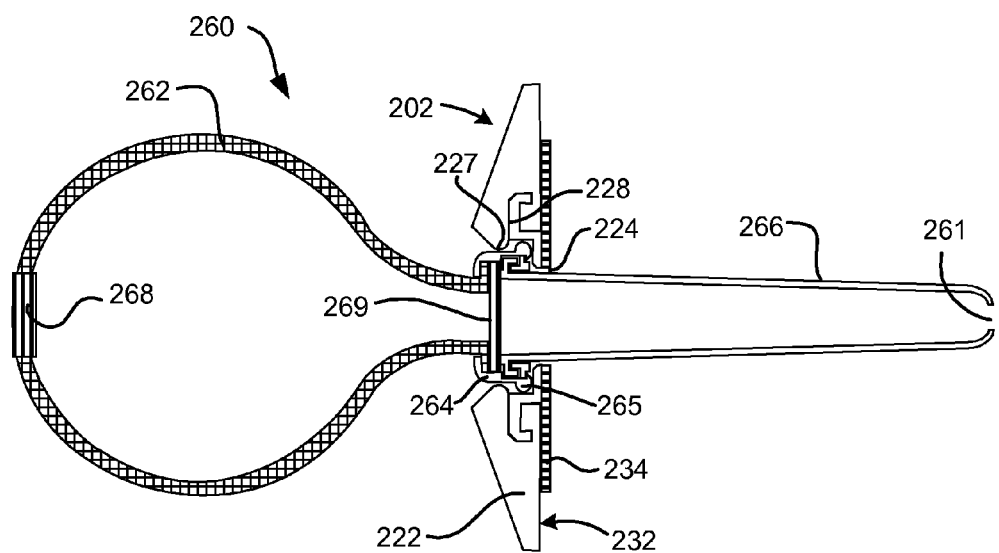
FIG. 2D shows a sectional view of the pneumostoma aspirator of FIG. 2C mated with the pneumostoma management device of FIGS. 2A and 2B according to an embodiment of the present invention.

FIGS. 2A through 2D illustrate views of a pneumostoma management system including a pneumostoma management device ("PMD") 201 and a pneumostoma aspirator 260 in accordance with an embodiment of the present invention. FIGS. 2C and 2D show pneumostoma aspirator 260 and its interaction with the PMD 201. Referring first to FIGS. 2A and 2B, PMD 201 includes a chest mount 202 which may be mounted to the skin of the patient and a pneumostoma vent 204 which is fitted to the chest mount 202. In a preferred embodiment, pneumostoma vent 204 is mounted through an aperture 224 in chest mount 202. Chest mount 202 has a first coupling that engages a second coupling of the pneumostoma vent to releasably secure the pneumostoma vent 204 to the chest mount 202. As will be further described below, the join between the two components of PMD 201 is engineered to ensure that pneumostoma vent 204 cannot be over-inserted into the lung if it separates from chest mount 202.

As shown in FIGS. 2A and FIG. 2B, pneumostoma vent 204 includes a tube 240 sized and configured to fit within the channel of a pneumostoma 110. Tube 240 is stiff enough that it may be inserted into a pneumostoma without collapsing. Over time, a pneumostoma may constrict and it is one function of PMD 201 to preserve the patency of the channel of the pneumostoma by resisting the natural tendency of the pneumostoma to constrict. Tube 240 of pneumostoma vent 204 preferably comprises an atraumatic tip 252 at the distal end. (This application uses the terms proximal and distal regarding the components of the pneumostoma management system in the conventional manner. Thus, proximal refers to the end or side of a device closest to the hand operating the device, whereas distal refers to the end or side of a device furthest from the hand operating the device.) Tip 252 may be rounded, beveled or curved in order to reduce irritation or damage to the tissues of the pneumostoma or lung during insertion or while in position. Opening 254 in tip 252 allows the entry of gases from the cavity of the pneumostoma 110 into lumen 258 of tube 240. Tube 240 is optionally provided with one or more side openings (not shown) positioned near tip 252 and/or along the length of tube 240 to facilitate the flow of gas and/or mucous/discharge into lumen 258.

Tube 240 of pneumostoma vent 204 is sufficiently long that it can pass through the thoracic wall and into the cavity of a pneumostoma inside the lung. Pneumostoma vent 204 is not however so long that it penetrates so far into the lung that it might cause injury. The material and thickness of tube 240 of pneumostoma vent 204 is selected such that tube 240 is soft enough that it will deform rather than cause injury to the pneumostoma or lung. Pneumostoma vent 204 has an opening 254 in tip 252 of tube 240. The length of tube 240 required for a pneumostoma vent 204 varies significantly between different pneumostomas. A longer tube 240 is usually required in patients with larger amounts of body fat on the chest. A longer tube 240 is usually required where the pneumostoma is placed in the lateral position 112 rather than the frontal position 110. Because of the variation in pneumostomas, pneumostoma vents 204 are manufactured having tubes 240 in a range of sizes and a patient is provided with a pneumostoma vent 204 having a tube 240 of appropriate length for the patient's pneumostoma.

Pneumostoma vent 204 includes a cap 242 and a hydrophobic filter 248 over the opening 255 in the proximal end of tube 240. Hydrophobic filter 248 is positioned over the proximal opening 255 into lumen 258. Hydrophobic filter 248 is positioned and mounted such that material moving between lumen 258 and the exterior of pneumostoma vent 204 must pass through hydrophobic filter 248. Hydrophobic filter 248 is preferably designed such to fit into a recess in cap 242. As shown in FIG. 2B, cap 242 comprises a recess 238 into which hydrophobic filter 248 may be fit. Hydrophobic filter 248 may alternatively be fitted into cap 242 using a joint such as a threaded coupling or adhesive or, in some cases, formed integrally with cap 242. Hydrophobic filter 248 may be made from a material such as medical grade GOR-TEX (W. L. Gore & Associates, Inc., Flagstaff, Ariz.). As shown in FIG. 2B, a snap ring 243 locks cap 242 and hydrophobic filter 248 onto the proximal end of tube 240.

Hydrophobic filter 248 serves several purposes. In general, hydrophobic filter 248 controls the passage of solid or liquid material between the lumen 258 and the exterior of cap 242. For example, hydrophobic filter 248 prevents the flow of water into the lumen 258 through proximal opening 255. Thus, a patient using PMD 201 may shower without water entering the lung through the pneumostoma. Hydrophobic filter 248 may also be selected so as to prevent the entry of microbes, pollen and other allergens and pathogens into the lumen 258. Hydrophobic filter 248 also prevents the exit of liquid and particulate discharge from lumen 258 to the exterior of pneumostoma vent 204. This is desirable to prevent contact between liquid and particulate discharge and clothing for example.

Chest mount 202 connects to the proximal end of pneumostoma vent 204. In one embodiment, illustrated in FIGS. 2A and 2B, chest mount 202 comprises a flange 222 and an aperture 224. The aperture 224 is adapted and configured to receive the pneumostoma vent 204. Chest mount 202 is designed to have a smooth surface and a low profile so it is comfortable for the patient to wear. Chest mount 202 should be designed so as not to snag on the patient's clothing or to restrict motion of the patient's arm (if placed in a lateral pneumostoma 112). Flange 222 is significantly wider than pneumostoma vent 204. Flange 222 thus comprises a contact surface 232 which contacts the skin of the patient surrounding the pneumostoma and positions the aperture 224 over the opening of the pneumostoma. Flange 222 is designed such that it is sufficiently flexible that it can conform to the surface of the chest. Contact surface 232 is also provided with a pad of biocompatible adhesive 234, such as a hydrocolloid adhesive, for securing flange 222 to the skin of the patient. The adhesive 234 may be protected by a protector sheet that is removed prior to use of flange 222. Adhesive 234 should be selected so as to secure flange 222 to the chest of the patient in the correct position relative to the pneumostoma without causing undue irritation to the skin of the patient. The adhesive need not create an air tight seal between flange 222 and the skin of the patient. Suitable adhesive pads are available commercially from Avery Dennison (Painesville, Ohio).

Referring now to FIG. 2A which shows a perspective view of chest mount 202 after insertion of pneumostoma vent 204. Flange 222 is generally circular but is provided with one or more tabs 236 to facilitate application and removal of flange 222 from the skin of the patient. As shown in FIG. 2A, chest mount 202 comprises an aperture 224 through which tube 240 of pneumostoma vent 204 may be inserted. Flange 222 is slightly convex on the upper surface 235. Flange 222 includes a recess 226 into which cap 242 of pneumostoma vent 204 may be press fit. Flange 222 is thick enough in the region of aperture 224 to receive the cap 242 of pneumostoma vent 204 so that the cap of pneumostoma vent 204 is flush with the upper surface 235 of flange 222. Recess 226 forms a coupling adapted to releasably secure the cap 242 of pneumostoma vent 204 into flange 222. As shown in FIG. 2B, recess 226 has a lip 227 to releasably secure the cap 242 of pneumostoma vent 204 into flange 222. However, other couplings may be used to releasably secure pneumostoma vent 204 to chest mount 202 including clips, pins, snaps, catches, threaded joints, temporary adhesive and the like. Cap 242 is attached to the proximal end of tube 240. Hydrophobic filter 248 is sandwiched between cap 242 and tube 240. An opening 244 in cap 242 communicates with the lumen 258 of tube 240 via hydrophobic filter 248. As shown in FIGS. 2A and 2B, cap 242 comprises a lip 246 which releasably engages lip 227 of recess 226 of flange 222 to secure pneumostoma vent 204 within the recess 226 of flange 222. Lip 246 forms a coupling element of pneumostoma vent 204 that cooperates with recess 226 to releasably secure pneumostoma vent 204 into chest mount 202 with tube 240 positioned through aperture 224.

In a preferred embodiment, an aperture plate 228 is embedded in the conformable polymer of flange 222. The aperture plate 228 defines aperture 224 of chest mount 202. Aperture plate 228 is made of a stiffer, less compliant material than flange 222 in order that the dimensions of aperture 224 are tightly controlled. Aperture plate 228 is stiff enough that the size and shape of aperture 224 remains stable even under any reasonably possible application of force to chest mount 202. It should be noted that the outer diameter of each of snap ring 243, hydrophobic filter 248, flange 241 and cap 242 is larger than the diameter of aperture 224 of aperture plate 228. Thus, snap ring 243, hydrophobic filter 248, flange 241 and cap 242 cannot pass through aperture 224 into the pneumostoma 110. Distal tip 252 of tube 240 and the body of tube 240 are small enough to pass through aperture 224 however, flange 241 and/or cap 242 serve to limit the passage of tube 240 through aperture 224. These safety features prevent unsafe entry of any of the components of pneumostoma vent 204 into pneumostoma even in the unlikely event of damage to the device. Likewise all the components of the chest mount 202 such as flange 222 and aperture plate 224 are significantly larger than the aperture of a pneumostoma thus precluding passage of any component of the chest mount 202 into a pneumostoma even in the unlikely event of damage to the device.

Referring now to FIGS. 2C and 2D which show a pneumostoma aspirator adapted for use with PMD 201 of FIGS. 2A and 2B as part of pneumostoma management system. FIG. 2C shows a perspective view of pneumostoma aspirator 260. FIG. 2D shows a sectional view through pneumostoma aspirator 260 of FIG. 2C when mounted in a chest mount 202. As shown in FIGS. 2C and 2D, pneumostoma aspirator 260 includes a bulb 262 a coupling 264 and a tube 266. Tube 266 has an opening 261 in the distal end. Opening 261 is adapted to allow entry of gases as well as solid and liquid discharge during operation of aspirator. Tube 266 may be provided with additional openings is the side of tube 266. Pneumostoma aspirator is configured such that tube 266 may be inserted through aperture 224 of chest mount 202 into a pneumostoma. Tube 266 is sufficiently long to enter the pneumostoma but is not so long that it might cause injury to the pneumostoma. Coupling 264 is designed such that it is too large to pass through aperture 224 of the aperture plate 228 of chest mount 202 thereby preventing further insertion of tube 266 into a pneumostoma. Coupling 264 may also be provided with a feature such as a lip 265 for releasably engaging lip 227 of recess 228 of chest mount 202. Bulb 262 is made of a flexible material such that it may be squeezed to reduce the volume of the bulb and when released will return to its previous volume. The re-expansion of bulb 262 may be utilized to apply suction to the pneumostoma to remove fluid and/or discharge. In some embodiments, the reduction in volume of bulb 262 may be used to push the contents of bulb 262 into a pneumostoma, for example an irrigating fluid such as sterile saline or water.

As shown in FIG. 2D, pneumostoma aspirator 260 optionally comprises a one-way valve 268 through which air may pass out of bulb 262. In some embodiments, pneumostoma aspirator 260 may also include a one-way valve 269 configured to allow material to flow from tube 266 into bulb 262. Valve 268 allows air to escape bulb 262 when it is compressed. Thus, valves 268 and 269 prevent air flow into the pneumostoma. In this way device 260 may be designed to provide suction alone instead of suction and irrigation. In some embodiments, it may be desirable to prevent pneumostoma aspirator 260 from expelling material into the pneumostoma. In a simple embodiment, an aperture may be provided in bulb 262 in place of valve 268. The aperture is configured to allow air to escape when bulb 262 is squeezed. The aperture may then be covered with a digit so that air may not enter the aperture when bulb 262 expand and is instead drawn from the pneumostoma through tube 266.

A range of pneumostoma aspirators may be manufactured each having a size appropriate for a different pneumostoma. To simplify manufacture, pneumostoma aspirator 260 may be designed to use some components in common with pneumostoma vent 204. For example, the range of tubes 240 of the pneumostoma vent 204 may be used as tube 266 of pneumostoma aspirator 260. In some embodiments, the cap 264 may also be a shared component. Thus the only additional components required for pneumostoma aspirator 260 are bulb 262 and (optionally) valves 268 and 269. Alternatively the pneumostoma aspirator 260 may be made in only one size where the single size of tube 266 is short enough so as not to cause injury even in a small pneumostoma.

Figure 2E:
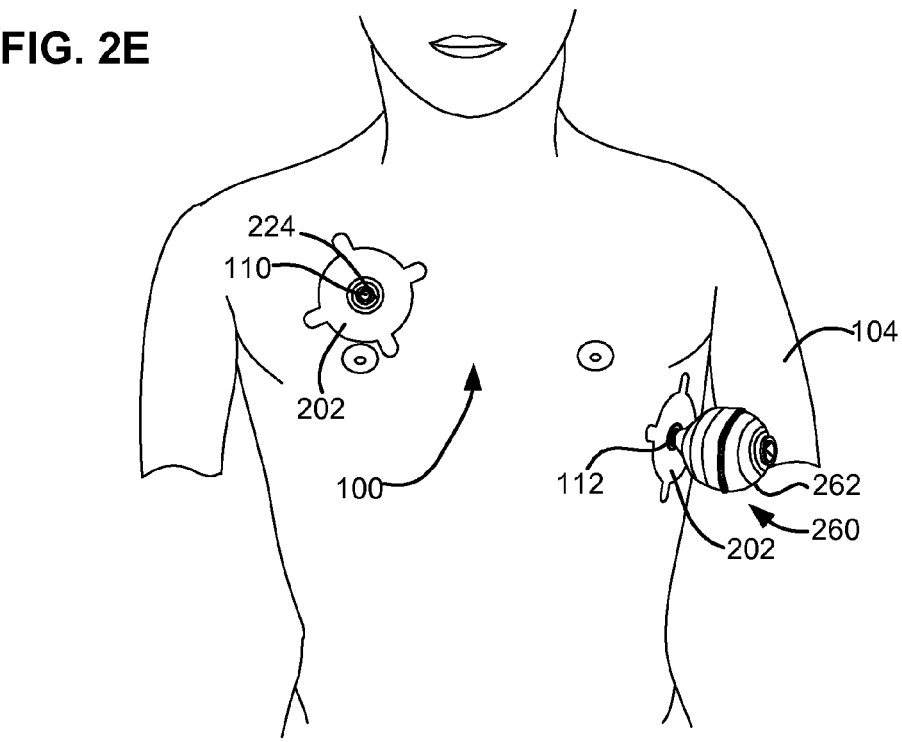
FIG. 2E shows a positioning of a pneumostoma management device and pneumostoma aspirator relative to the chest of a patient.

FIG. 2E illustrates the positioning of pneumostoma aspirator 260 over pneumostoma 112 of FIG. 1A. In a preferred embodiment, the chest mount 202 remains attached for up to a week thereby avoiding irritation of the skin caused by daily attachment and removal of a mount. Chest mount may be positioned by the patient by manual alignment of the aperture 224 of chest mount 202 with the aperture of the pneumostoma 112. To use pneumostoma aspirator 260, chest mount 202 is first positioned over a pneumostoma and secured with adhesive to the skin of the patient. Alternatively, a pneumostoma vent or an alignment tool may be used to align the chest mount. Pneumostoma aspirator 260 is then inserted through the aperture in the chest mount until it engages the chest mount 202. As shown in FIG. 2E the pneumostoma aspirator 260 is inserted through chest mount 202 after pneumostoma vent 204 has been removed. Pneumostoma aspirator 260 is then used to apply suction to pneumostoma 112 by manual operation of bulb 262 either by the patient, caregiver or medical practitioner. The application of suction draws discharge from the pneumostoma into the aperture 261 at the distal end of the aspirator 260. Where suction is applied care should be taken to remove any discharge collected to prevent reentry of discharge into the pneumostoma 112.

Figure 2F:
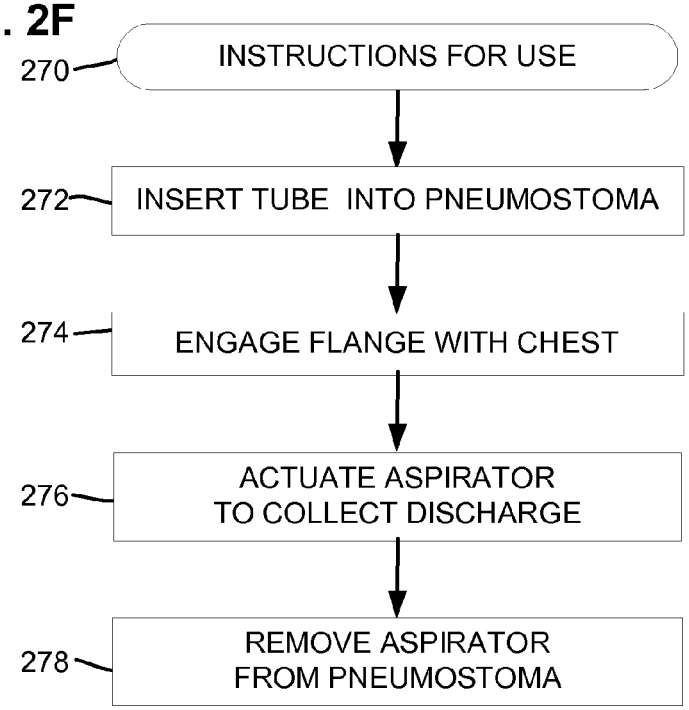
FIG. 2F shows a method of using a pneumostoma aspirator in accordance with an embodiment of the present invention, in the form of instructions for use.

FIG. 2F illustrates a method for using a pneumostoma aspirator according to an embodiment of the present invention. The method is illustrated in the form of Instructions For Use 270. Instructions For Use are provided to patients with a medical device such as a pneumostoma aspirator. Referring to FIG. 2F the instructions from use include instructions to perform the following steps. At step 272 the tube of the pneumostoma aspirator is inserted into the pneumostoma. At step 274 the tube is pushed into the pneumostoma until the flange of the aspirator engages the chest of the patient and prevents further insertion. At step 276 the aspirator is actuated to collect discharge in the tube. For example, the bulb is squeezed and then allowed to expand sucking air and discharge into the tube. Alternatively the plunger on a syringe is pulled back sucking air and discharge into the tube. Finally at step 278 the aspirator is withdrawn from the pneumostoma. The discharge may then be eliminated. The instructions will be slightly different where the aspirator is designed to operate with a chest mount already in place. In such case, the flange is already engaged with the chest and insertion of the aspirator is limited by engagement of the aspirator with the flange of the chest mount.

In some embodiments, pneumostoma aspirator 260 may alternatively or additionally be used to apply irrigation to pneumostoma 112 by manual operation of bulb 262 either by the patient, caregiver or medical practitioner. For irrigation, a sterile but inert solution may be used. For example, sterile saline or sterile water may be used. Alternatively, an antibacterial or mucolytic solution may be used. The cleaning solution may also include a small concentration of an agent for maintaining the patency of the pneumostoma for example, Paclitaxel. The cleaning solution should be formulated carefully to avoid injury or irritation to the lung. The pneumostoma aspirator can be used to push the irrigation fluid through the aperture 261 in the distal end of the aspirator and into the pneumostoma.

Alternative Pneumostoma Aspirators

Figure 3A:
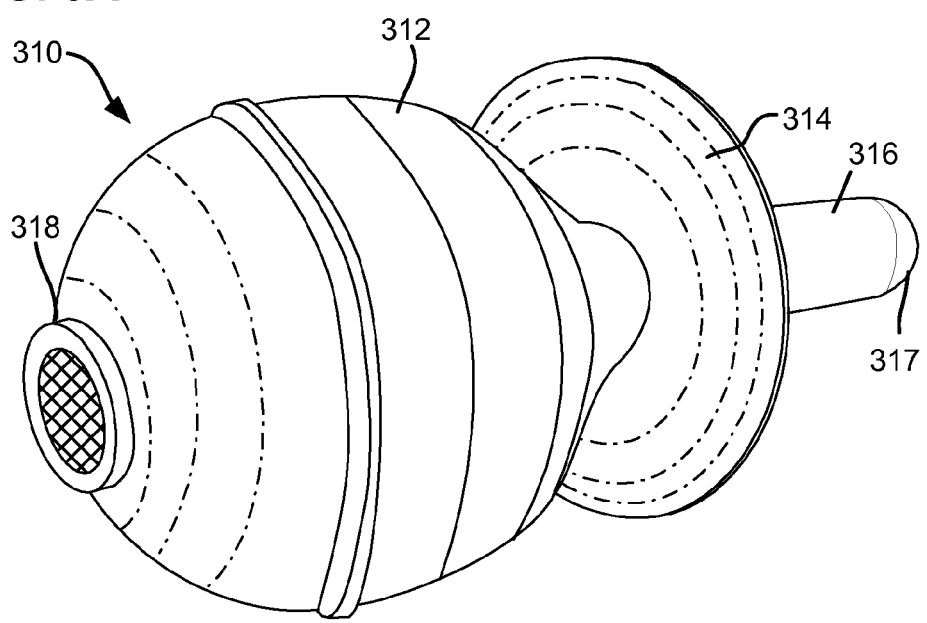
FIG. 3A shows a perspective view of an alternative pneumostoma aspirator according to an embodiment of the present invention.
Figure 3B:
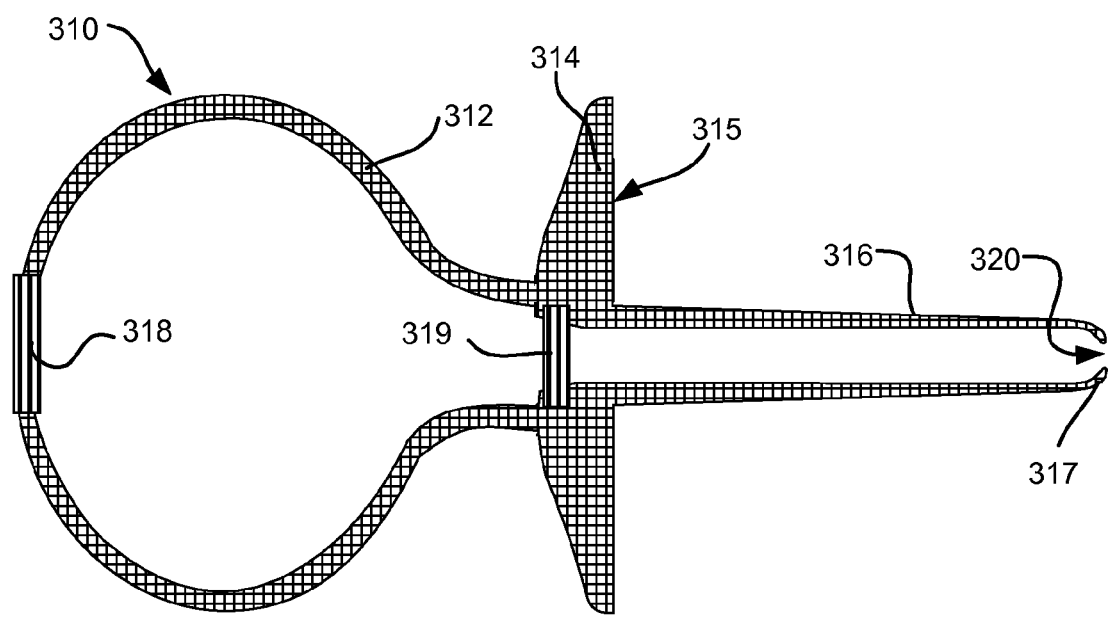
FIG. 3B shows a sectional view of the pneumostoma aspirator of FIG. 3A.

FIGS. 3A and 3B show an alternative pneumostoma aspirator 310 designed to apply suction to a pneumostoma. FIG. 3A shows a perspective view of pneumostoma aspirator 310. FIG. 3B shows a sectional view of the pneumostoma aspirator 310. As shown in FIGS. 3A and 3B, pneumostoma aspirator 310 includes a flexible bulb 312 attached to a flange 314 which is attached to a tube 316. Tube 316 has an opening 320 in the distal end. Opening 320 is adapted to allow entry of gases as well as solid and liquid discharge during operation of aspirator 310. Tube 316 may also be provided with additional openings in the side of tube 316. Tube 316 of aspirator 310 preferably has an atraumatic tip 317 at the distal end to prevent injury and/or irritation to the pneumostoma during insertion.

Flange 314 attached to tube 316 is significantly larger than the diameter of tube 316. Flange 314 is too large to enter a pneumostoma and thus acts as a stop to prevent further insertion of tube 316 when flange 314 makes contact with the skin of the patient's chest. The contact surface 315 of flange 314 may also be used to make a temporary seal surrounding the pneumostoma so that when applying suction to the pneumostoma there is reduced leakage of air/fluid around tube 316. Contact surface 315 may be provided with surface features (for example ridges) to enhance the formation of a temporary seal between flange 314 and the skin of the chest.

Tube 316 extends far enough past flange 314 so that it can pass through the thoracic wall into the pneumostoma. Tube 316 is not, however, so long that it may cause injury to the pneumostoma or lung. The maximum desirable length of tube 316 varies significantly between different pneumostomas. A longer tube 316 may be desirable in patients with larger amounts of body fat on the chest. A longer tube 316 may also be desirable where the pneumostoma is placed in the lateral position 112 rather than the frontal position 110. Because of the variation in pneumostomas, pneumostoma aspirators 310 may be manufactured having tubes 316 in a range of sizes. A patient can thus be provided with a pneumostoma aspirator 310 having a tube 316 of appropriate length for the patient's pneumostoma. Tube 316 may be from 30 mm to 120 mm in length and from 5 mm to 20 mm in diameter depending on the size of a pneumostoma. A typical tube 240 may be between 40 mm and 80 mm in length and between 8 mm and 12 mm in diameter. In alternative embodiments, a pneumostoma aspirator is made with a tube 316 of a single length (such as 120 mm) and tube 316 is then cut to the length appropriate for a particular patient. In alternative embodiments, a pneumostoma aspirator is made with a tube 316 of a single short length (such as 30 mm) which can be used in any pneumostoma without causing injury.

As shown in FIGS. 3A and 3B, bulb 312, flange 314 and tube 316 of pneumostoma aspirator 310 are made in one piece. They may alternatively be formed separately and then joined by welding, gluing or otherwise bonding/connecting. Suction irrigation device 310 may also comprise valves 318 and 319. Valves 318 and 319 are flow control devices (for example flapper valves) which allow flow in on one direction only. Thus, where pneumostoma aspirator 310 is a suction device, valves 318 and 319 may be present and configured such that, when bulb 312 is compressed air leaves bulb 312 only via valve 318, and when bulb 312 is released air enters bulb 312 only via tube 316. In this way materials are drawn out of the pneumostoma. Note that, for safety reasons, the components of valves 318 and 319 are too large to fit through tube 316 and thus cannot be aspirated into the lung even in the event of damage to pneumostoma aspirator 310. For ease of assembly, valves 318 and 319 are press fit into recesses in bulb 312. Valve 319 (if present) is smaller than valve 318 so that valve 319 can be inserted into bulb 312 through the aperture for mounting valve 318.

Pneumostoma aspirator may be used in accordance with the instructions for use of FIG. 2F. However, the patient/caregiver should be instructed to remove the pneumostoma management device from the pneumostoma prior to step 272. Also, after step 278, the patient/caregiver should be instructed to promptly place a new pneumostoma management device into the pneumostoma.

Figure 4B:
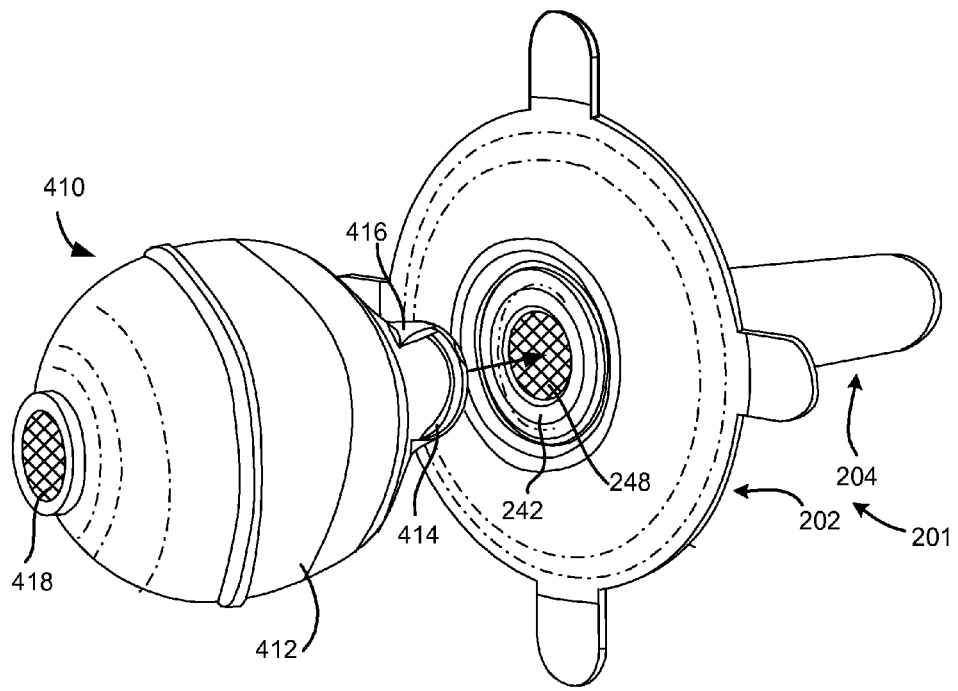
FIG. 4B shows a sectional view of the pneumostoma aspirator of FIG. 3A.
Figure 4B:
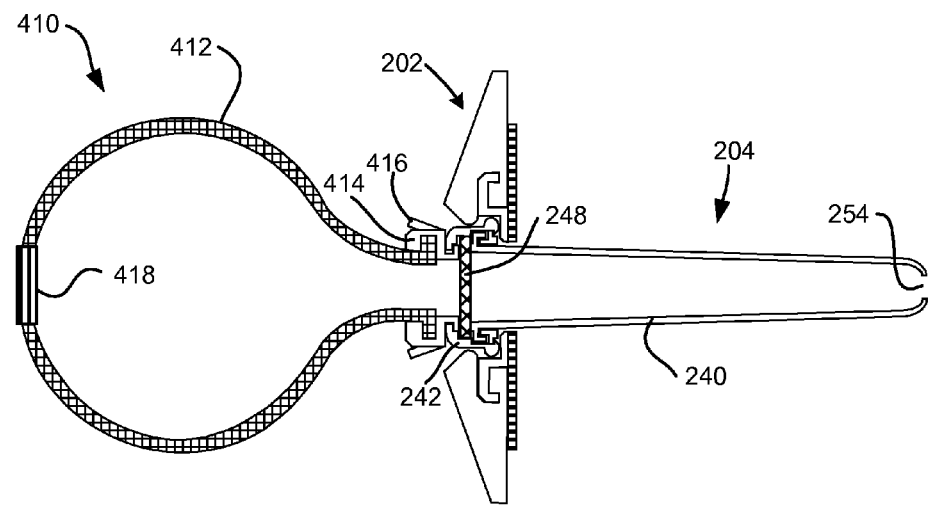

FIGS. 4A and 4B show an alternative pneumostoma aspirator 410 designed to apply suction to a pneumostoma. The pneumostoma aspirator 410 operates in conjunction with a pneumostoma management device located within a pneumostoma e.g. PMD 200 of FIGS. 2A-2E. FIG. 4A shows a perspective view of aspirator 410. FIG. 4B shows a sectional view of aspirator 410. As shown in FIGS. 4A and 4B, aspirator 410 includes a flexible bulb 412 attached to a coupling 414 which has two releases 416. Aspirator 410 also has a one-way valve 418 for releasing air from bulb 412. Coupling 414 is designed to releasably attach to cap 242 of pneumostoma vent 204. Releases 416 are release mechanisms which may be operated to release coupling 414 from cap 242 in order to reuse aspirator 410. In an alternative embodiment, aspirator 410 is a single-use device and coupling 414 permanently attaches to cap 242—releases 416 are therefore absent.

FIG. 4A shows aspirator 410 aligned for attachment to cap 242 of pneumostoma vent 204. FIG. 4B shows aspirator 410 after it has been attached to cap 242.

The aspirator 410 of FIGS. 4A and 4B may be used at the time of removal of pneumostoma vent 204 in order to remove discharge from the pneumostoma prior to replacement of pneumostoma vent 204. As shown in FIG. 4B, when coupling 414 attaches to cap 242, sufficient seal is made that suction can be applied to pneumostoma vent 204 by aspirator 410. Valve 418 is a flow control device (for example flapper valve) which allows flow in one direction only. Thus, when bulb 412 is compressed, air leaves bulb 412 via valve 418, and when bulb 412 is released, air enters bulb 412 only via pneumostoma vent 204. In this way, materials are drawn out of the pneumostoma through aperture 254 and into pneumostoma vent 204. In the embodiment of FIGS. 4A, 4B, the discharge will accumulate in tube 240 of pneumostoma vent 204 because it cannot pass through the hydrophobic filter 248. In alternative embodiments, hydrophobic filter 248 may be absent or removed and discharge may be withdrawn directly into bulb 412. After applying suction to pneumostoma vent 204, aspirator 410 (or another device) can be used to remove the pneumostoma vent 204 (containing the discharge). Thus aspirator 410 may serve as a combination of aspirator and pneumostoma vent removal tool. A new pneumostoma vent 204 may be inserted in chest mount 202 after removal of the old pneumostoma vent.

Figure 4C:
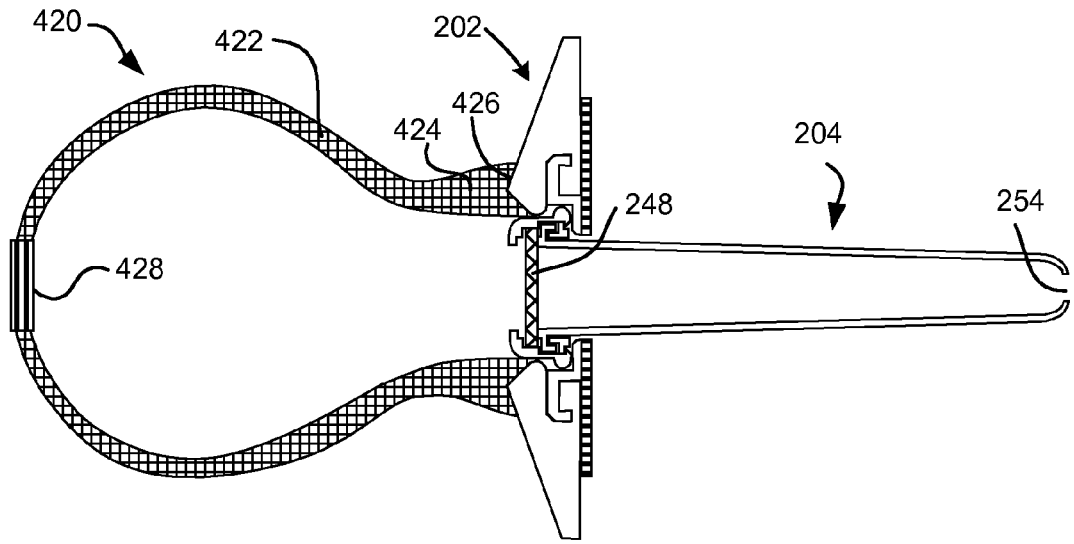
FIG. 4C shows a sectional view of an alternative pneumostoma aspirator according to an embodiment of the present invention.

In alternative embodiments, an aspirator 420 is designed to mate with chest mount 202 instead of or in addition to pneumostoma vent 204. For example, as shown in FIG. 4C, bulb 422 has a mating section 424, having a mating surface 426 designed to mate and make a temporary seal with the exterior surface of chest mount 202. In use, aspirator 420 is pushed against chest mount 202 to make a temporary seal. Bulb 422 is then compressed, expelling air through one-way valve 428. Bulb 422 is then released such that it expands and withdraws air and discharge into/through aperture 254 in the distal end of pneumostoma vent 204. The discharge collects inside tube 240 of pneumostoma vent 204. After applying suction to pneumostoma vent 204, pneumostoma vent 204 (containing the discharge) may be removed and disposed of. A new pneumostoma vent 204 may then be inserted in chest mount 202. In the embodiment shown in FIG. 4C, bulb 422 is held in contact with chest mount 202 in order to make a temporary seal during aspiration of the pneumostoma.

Figure 4D:
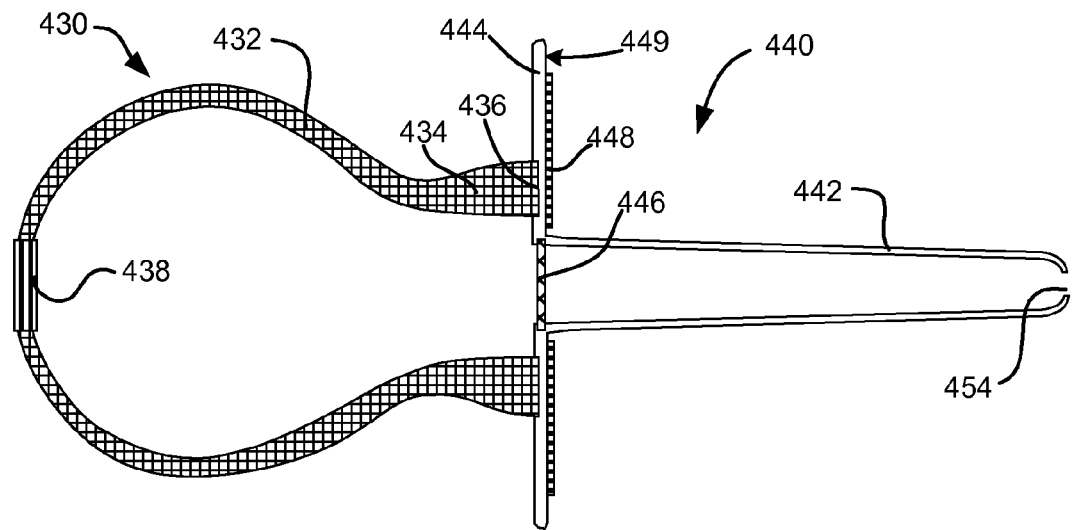
FIG. 4D shows a sectional view of an alternative pneumostoma aspirator according to an embodiment of the present invention.

FIG. 4D illustrates another embodiment having an aspirator 430 designed to mate with a PMD 440 in which tube 442 is formed in one piece with (or permanently attached to) a flange 444. PMD 440 has a hydrophobic filter 446 press fit into the proximal end of tube 442 and has a biocompatible adhesive 448 on the contact surface 449 of flange 444 for releasably securing flange 444 to the skin of the patient's chest. As shown in FIG. 4D, aspirator 430 includes a bulb 432 which has a mating section 434, having a mating surface 436 designed to mate and make a temporary seal with the exterior surface of flange 444. In use, aspirator 430 is pushed against flange 444 to make a temporary seal. Bulb 432 is then compressed, expelling air through one-way valve 438. Bulb 432 is then released such that it expands and withdraws air and discharge into/through aperture 454 in the distal end of tube 442 of PMD 440. The discharge collects inside tube 442 of PMD 440. After applying suction to PMD 440, PMD 440 (containing the discharge) may be removed. A new PMD 440 may then be inserted into the pneumostoma.

In the previous embodiments, a flexible bulb (with or without one or more valves) has been provided as the mechanism by which irrigation fluid may be provided or suction applied. In alternative designs a different mechanism may be provided to produce the negative pressure required to extract the fluid/air discharge from the pneumostoma. Such mechanisms include vacuum bottles, pumps, fans and syringes. (Or positive pressure for irrigation). In each case it is desirable that the mechanism have safety features to prevent over insertion of any component into the pneumostoma or the application of positive or negative pressure sufficient to cause injury to the lung. The safety features are particularly desirable in devices intended for use by the patient rather than a trained medical professional.

Figure 5:
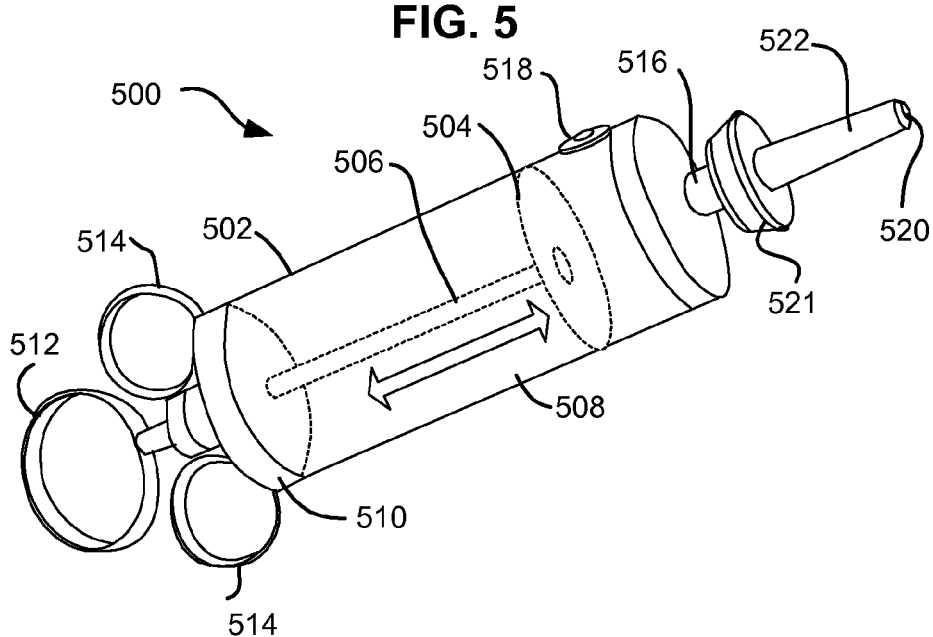
FIG. 5 shows a perspective view of an alternative pneumostoma aspirator according to an embodiment of the present invention.

FIG. 5 illustrates an alternative embodiment of a pneumostoma aspirator 500 in which the positive and/or negative pressure is applied using a syringe 502. Syringe 502 includes a plunger 504 which can be pushed and pulled by a rod 506 within barrel 508. Rod 506 passes though cap 510 to ring 512 which may be manually operated to move plunger 504. Rings 514 are connected to cap 510 which is connected to barrel 508. As plunger moves up and down in barrel 508 the volume of the space in the barrel distal of plunger 504 is changed applying negative positive or negative pressure. Positive pressure can be used to push irrigating fluid through aperture 520 of nozzle 516 into a pneumostoma. Negative pressure can be used to withdraw fluid, discharge and/or air through aperture 520 of nozzle 516 from the pneumostoma into barrel 508. Note that in this embodiment, a safety valve 518 is provided which opens in the event that the positive or negative pressure is outside of a preset safe range. Furthermore, nozzle 516 comprises a coupling 521 for engaging a chest mount 202 as shown in FIGS. 2A-2E. A tube 522 extends distal of coupling 521 for insertion in the pneumostoma, but coupling 521 limits the depth of insertion of tube 522. In alternative embodiments, nozzle 516 may comprise a flange for preventing over-insertion or mating devices for coupling the syringe to part of a PMD including for example, a chest mount 202 or pneumostoma vent 204 as described above. For example, syringe 502 may be used, with appropriate adaptations, in place of the bulb in the embodiments of FIGS. 2C-E, 3A-B and 4A-D. Pneumostoma aspirator 500 may be a sterilizable reusable device made, for example, from stainless steel and/or glass components. Pneumostoma aspirator 500 may alternatively be a disposable device made, for example, from medical grade plastics.

Figure 6:
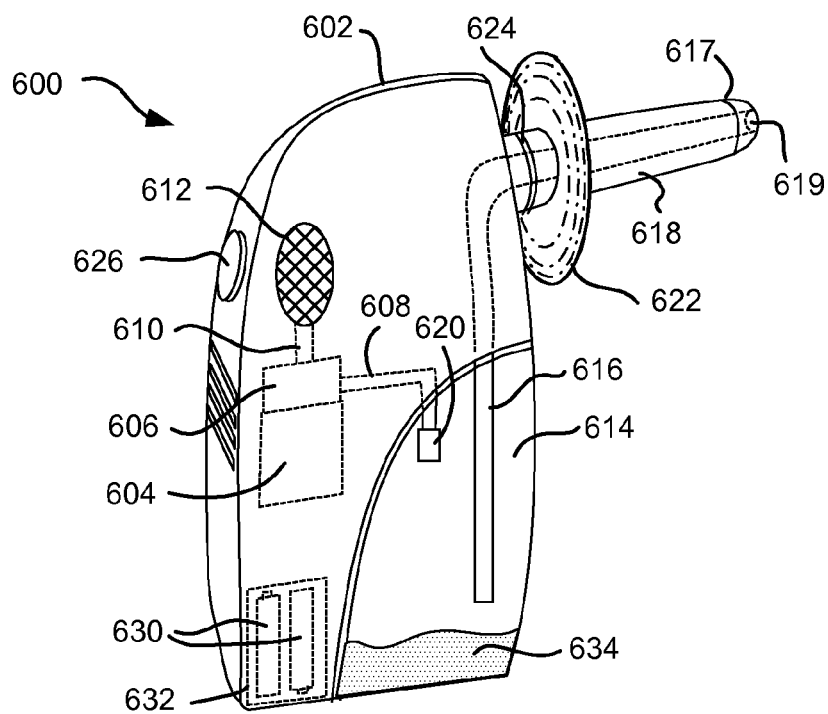
FIG. 6 shows a perspective view of a motorized alternative pneumostoma aspirator according to an embodiment of the present invention.

FIG. 6 illustrates an alternative embodiment of a pneumostoma aspirator 600 in which the positive and/or negative pressure is applied using a motorized device 602. Motorized device 602 includes a motor 604 which turns a fan/pump 606. The power for motor 604 may be provided by batteries 630 in battery housing 632. Batteries 630 may be rechargeable batteries. Fan/pump 606 draws air in through tube 608 and expels it through tube 610 and vent 612. Tube 608 terminates inside removable reservoir 614. Thus operation of fan/pump 606 creates negative pressure inside reservoir 614. Tube 616 connects reservoir 614 to tube 618 which is adapted to enter a pneumostoma. Tube 618 has an atraumatic tip 617 to facilitate insertion into a pneumostoma and one or more apertures 619 in the tip through which air and discharge may enter tube 618 to be sucked via tube 616 into reservoir 614.

Note that the end of tube 608 has a valve/filter 620 which prevents entry of discharge into tube 610 and fan/pump 606. Vent 612 may also be provided with a replaceable filter (for example a HEPA filter) to prevent the venting of any pathogens which may be in the gases extracted from the lung. Fan/pump 606 is selected so that it is self-limiting as to the maximum negative pressure it is capable of producing in reservoir 614. The maximum negative pressure is selected to be at a level which will not damage the pneumostoma or lung.

A safety valve may additionally or alternatively be provided which opens in the event that the pressure is outside of a preset safe range. Reservoir 614 is preferably translucent so that accumulation of discharge may be observed.

Tube 618 is connected with a flange 622 which limits the depth of insertion of tube 618 into a pneumostoma. In alternative embodiments, tube 618 may comprise a coupling for engaging a chest mount 202 as shown in FIGS. 2A-2E. Tube 618 extends distal of flange 622 for a distance selected so as not to damage a pneumostoma. Different lengths of tube 618 may be supplied depending on the size of pneumostoma in a particular patient. A coupling 624 (for example, a threaded joint or slip-on fitting) may allow the tube 618 and flange 622 to be removed and replaced.

In operation, tube 618 is pushed into the pneumostoma until flange 622 engages the chest of the patient to prevent further insertion. The patient (or medical provider) then pushes button 626 which actuates motor 604. Motor 604 drives fan/pump 606 which extracts air from reservoir 614. Air is sucked through tube 618 via tube 616 into reservoir 614. Solid and liquid discharge may also be sucked through the aperture(s) in the tip of tube 618 and thence into reservoir 614. The discharge 634 accumulates in reservoir 614. Gases removed from the pneumostoma are vented through vent 612. After sufficient discharge has been removed from the pneumostoma, the pneumostoma aspirator is removed from the pneumostoma. Reservoir 614 may be then detached from motorized device 602, emptied, cleaned and re-attached. Alternatively, reservoir 614 may be disposable, in which case, the reservoir is detached, disposed of and replaced with a new reservoir. Likewise tube 618 may be detached and cleaned or detached and replaced. Motorized device 602 is preferable a reusable device.

Although pneumostoma aspirator has been illustrated with a flange 622, it should be noted that alternative structures may be connected with motorized device 602 so that it may be coupled to a pneumostoma vent or chest mount as previously shown. For example, motorized device 602 may be used, with appropriate adaptations, in place of the bulb in the embodiments of FIGS. 2C-E, 3A-B and 4A-D.

Materials

In preferred embodiments, the pneumostoma management device and the pneumostoma aspirator are formed from biocompatible polymers or biocompatible metals. A patient will typically wear the PMD at all times and thus the materials, particularly of tubes entering the pneumostoma, should meet high standards for biocompatibility. In general preferred materials for manufacturing the suction irrigation device and the PMD are biocompatible thermoplastic elastomers that are readily utilized in injection molding and extrusion processing. As will be appreciated, other suitable similarly biocompatible thermoplastic or thermoplastic polymer materials can be used without departing from the scope of the invention. Biocompatible polymers may be selected from the group consisting of polyethylenes (HDPE), polyvinyl chloride, polyacrylates (polyethyl acrylate and polymethyl acrylate, polymethyl methacrylate, polymethyl-coethyl acrylate, ethylene/ethyl acrylate), polycarbonate urethane (BIONATEG), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyaryletheretherketone, polyetheretherketone, polyetherether-ketoneketone, polyetherketoneetherketoneketone polyetherketone), polyether block amides (PEBAX, PEBA), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers in general. Reference to appropriate polymers that can be used for manufacturing PMD 201 can be found in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the PMD include medical grade inorganic materials such stainless steel, titanium, ceramics and coated materials.

Hydrophobic filter 248 should be sufficiently porous to allow air to exit through the filter. Materials for hydrophobic filters are available commercially and filters can be fabricated from any suitable hydrophobic polymer, such as tetrafluoroethylene, PTFE, polyolefins, microglass, polyethylene and polypropylene or a mixture thereof. In preferred examples, the hydrophobic filter is a laminated tetrafluoroethylene e.g. TEFLON®, (E.I. du Pont de Nemours Co.) or GORE-TEX® (W.L. Gore, Inc.) of a controlled pore size. In other examples the hydrophobic filter may comprise a felted polypropylene; PTFE/polypropylene filter media. Hydrophobic filter 248 may additionally comprise an antimicrobial, an anti-bacterial, and/or an anti-viral material or agent.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. Embodiments of the present invention may use some or all of the features shown in the various disclosed embodiments where such features are not structurally or functionally incompatible. It is intended that the scope of the invention be defined by the claims and their equivalents.

What is claimed is:

1. A device for treating a pneumostoma which comprises a surgically-created aperture which passes through a chest wall of a patient and into a lung of a patient without communicating with a pleural cavity of the patient and which enables gases to exit the lung through the chest wall of the patient, the device comprising:
    a tube shaped for insertion into the pneumostoma, the tube having sufficient length that upon insertion into the pneumostoma, a proximal end of the tube is positioned exterior to a patient and a distal end of the tube is positioned within the lung of the patient;
    an aperture adjacent the distal end of the tube, the aperture sized and positioned to allow ingress of liquid and solid discharge from a lung;
    a lumen passing from the aperture to the proximal end of the tube;
    a flange projecting from the proximal end of the tube, the flange sized to prevent passage of the flange into the pneumostoma and thereby limit insertion of the tube into the lung; and
    a suction device connected to the proximal end of the tube such that, with the tube positioned in a pneumostoma and the flange positioned against the chest wall of the patient, actuation of the suction device applies negative pressure to the lumen at the proximal end of the tube and draws liquid and solid discharge from the lung into the lumen through the aperture adjacent the distal end of the tube.

2. The device of claim 1, wherein the suction device is a manually-actuated suction device.

3. The device of claim 2, wherein the suction device comprises an elastic bulb, such that, with the tube positioned in a pneumostoma and the flange positioned against the chest wall of the patient, the elastic bulb can be manually compressed and released, whereupon the elastic bulb expands and applies negative pressure to the lumen at the proximal end of the tube and draws liquid and solid discharge from the lung into the lumen through the aperture adjacent the distal end of the tube.

4. The device of claim 3, wherein a one-way valve is positioned through a surface of said elastic bulb such that, when the elastic bulb is manually compressed, gases within the elastic bulb are ejected exterior to the patient.

5. The device of claim 4, wherein a one-way valve is positioned between the lumen and the elastic bulb such that, when the elastic bulb is manually compressed, gases within the elastic bulb are prevented from entering the lumen of the tube.

6. The device of claim 5, wherein the tube, the flange and the elastic bulb are permanently connected.

7. The device of claim 6, wherein the tube, the flange, and the bulb are formed in one piece.

8. The device of claim 2, wherein the suction device comprises a syringe having a barrel and a plunger such that, with the tube positioned in a pneumostoma and the flange positioned against the chest wall of the patient, drawing the plunger distally within said barrel applies negative pressure to the lumen at the proximal end of the tube and draws liquid and solid discharge from the lung into the lumen through the aperture adjacent the distal end of the tube.

9. The device of claim 2, further comprising a safety device which limits the negative pressure applied to the lumen by the suction device.

10. The device of claim 2, wherein:
the flange and the tube are permanently connected;
the flange comprises a biocompatible adhesive positioned to releasably secure the flange to the chest wall of the patient;
and wherein the suction device further comprises a releasable coupling which releasably connects the suction device to the proximal end of the tube.

11. The device of claim 1 wherein the suction device comprises a battery-operated device including a motor coupled to one of a fan and a pump such that, with the tube positioned in a pneumostoma and the flange positioned against the chest wall of the patient, operation of the motor applies negative pressure to the proximal end of the tube and draws liquid and solid discharge from the lung into the lumen through the aperture adjacent the distal end of the tube.

12. A medical device for treating a pneumostoma which comprises a surgically-created aperture which passes through a chest wall of a chest of a patient and into a lung of a patient without communicating with a pleural cavity of the patient and which enables gases to exit the lung through the chest wall of the patient, the medical device comprising:
a flange sized and configured such that the flange cannot be inserted into the pneumostoma, the flange positioned to engage the chest of the patient;
a tube projecting from the flange, the tube configured such that, with the flange engaging the chest of the patient, the tube is positioned in the pneumostoma such that a proximal end of the tube is external to the patient and a distal end of the tube is positioned within the lung of the patient;
a lumen extending along the tube from the proximal end of the tube;
at least one aperture communicating with the lumen, the at least one aperture positioned such that, with the flange engaging the chest of the patient, the at least one aperture is positioned within the lung of the patient; and
a suction device connected to the proximal end of the tube such that, with the at least one aperture positioned within the lung of the patient, actuation of the suction device applies negative pressure to the lumen at the proximal end of the tube and draws liquid and solid discharge from the lung into the lumen through the at least one aperture.

13. The medical device of claim 12, wherein the suction device is a manually-actuated suction device.

14. The device of claim 12, wherein the suction device comprises an elastic bulb such that, with the at least one aperture positioned within the lung of the patient, the elastic bulb can be manually compressed and released whereupon the elastic bulb expands and applies negative pressure to the lumen at the proximal end of the tube and draws liquid and solid discharge from the lung into the lumen through the aperture adjacent the distal end of the tube.

15. The medical device of claim 12, wherein the suction device comprises a one-way valve and an elastic bulb such that, with the at least one aperture positioned within the lung of the patient, the elastic bulb can be manually compressed and released whereupon the elastic bulb expands and applies negative pressure to the lumen at the proximal end of the tube and draws liquid and solid discharge from the lung into the lumen through the aperture adjacent the distal end of the tube.

16. The medical device of claim 12, wherein the tube, the flange and the suction device are permanently connected.

17. The medical device of claim 12, wherein the suction device comprises a syringe having a barrel and a plunger such that, with the at least one aperture positioned within the lung of the patient, drawing the plunger distally within said barrel applies negative pressure to the lumen at the proximal end of the tube and draws liquid and solid discharge from the lung into the lumen through the aperture adjacent the distal end of the tube.

18. The device of claim 12, further comprising a safety device which limits the negative pressure applied to the lumen by the suction device.

19. The device of claim 12, wherein:
the flange and the tube are permanently connected;
the flange comprises a biocompatible adhesive positioned to releasably secure the flange to the chest wall of the patient;
and wherein the suction device further comprises a releasable coupling which releasably connects the suction device to the proximal end of the tube.

20. The device of claim 12, wherein the suction device comprises a battery-operated device including a motor coupled to one of a fan and a pump such that, with the at least one aperture positioned within the lung of the patient, operation of the motor applies negative pressure to the proximal end of the tube and draws liquid and solid discharge from the lung into the lumen through the aperture adjacent the distal end of the tube.

21. A system for treating a pneumostoma which comprises a surgically-created aperture which passes through a chest wall of a chest of a patient and into a lung of a patient without communicating with a pleural cavity of the patient and which enables gases to exit the lung through the chest wall of the patient, the system comprising:
- a pneumostoma management device which includes,
  - a flange sized and configured such that the flange cannot be inserted in the pneumostoma, the flange positioned to engage the chest of the patient,
  - a tube projecting from the flange, the tube configured such that, with the flange engaging the chest of the patient, the tube is positioned in the pneumostoma such that a proximal end of the tube is external to the patient and a distal end of the tube is positioned within the lung of the patient,
  - a lumen extending along the tube from the proximal end of the tube, and
  - an aperture communicating with the lumen, the aperture positioned such that, with the flange engaging the chest of the patient, the aperture is positioned within the lung of the patient; and
- a pneumostoma aspirator which includes,
  - a coupling configured to releasably secure the pneumostoma aspirator to the pneumostoma management device; and
  - a suction device connected to coupling such that, with the aperture positioned within the lung of the patient and the coupling releasably secured to the pneumostoma management device, actuation of the suction device applies negative pressure to the lumen at the proximal end of the tube and draws liquid and solid discharge from the lung into the lumen through the aperture.

22. The pneumostoma management system of claim 21, wherein the coupling is configured to releasably secure the pneumostoma aspirator directly to the flange of the pneumostoma management device.

23. The pneumostoma management system of claim 21, wherein the coupling is configured to releasably secure the pneumostoma aspirator directly to the tube of the pneumostoma management device.

24. The pneumostoma management system of claim 21, wherein the coupling has a self-seating and centering section which can mate with at least one of the of the tube and the flange of the pneumostoma management device.

25. The pneumostoma management system of claim 21, wherein the pneumostoma aspirator can self-seat against at least one of the tube and the flange of the pneumostoma management device.

* * * * *